United States Patent [19]

Hoag et al.

[11] Patent Number: 5,893,488

[45] Date of Patent: Apr. 13, 1999

[54] BONE CEMENT INJECTOR GUN

[75] Inventors: Stephen H. Hoag, Warsaw; Gregory C. Stalcup, Columbia City, both of Ind.; Kwan-Ho Chan, Lubbock, Tex.; Michael E. Hawkins, Columbia City; Kirt L. Case, Warsaw, both of Ind.

[73] Assignee: Bristol-Myers Squibb Co., New York, N.Y.

[21] Appl. No.: 08/877,324

[22] Filed: Jun. 17, 1997

Related U.S. Application Data

[63] Continuation-in-part of application No. 08/529,814, Sep. 18, 1995, Pat. No. 5,638,997.

[51] Int. Cl.$^6$ ........................................................ A67D 5/42
[52] U.S. Cl. .......................... 222/391; 222/327; 604/209; 606/94; 606/68; 606/234; 74/141.5; 74/169; 74/516; 74/522
[58] Field of Search ........................ 222/327, 391; 606/92, 93, 94, 95; 604/71, 181, 187, 207, 208, 209, 282, 73, 68, 232, 233, 234; 74/141.5, 169, 516, 522, 94

[56] References Cited

U.S. PATENT DOCUMENTS

| | | | |
|---|---|---|---|
| Re. 34,487 | 12/1993 | Keller | 222/327 X |
| D. 261,425 | 10/1981 | Bruhn | D24/26 |
| 546,073 | 9/1895 | Mix . | |
| 795,713 | 7/1905 | Letts | 222/391 X |
| 1,495,924 | 5/1924 | Quale | 604/232 |
| 2,224,967 | 12/1940 | Kaye | 259/47 |
| 2,305,238 | 12/1942 | Coates | 71/169 |
| 2,731,176 | 1/1956 | Crewe | 222/391 X |
| 2,732,102 | 1/1956 | Ekins | 222/327 |
| 2,750,943 | 6/1956 | Dann | 128/235 |
| 2,778,541 | 1/1957 | Sherbondy | 222/327 |
| 2,838,210 | 6/1958 | Detrie et al. | 222/327 |
| 3,053,457 | 9/1962 | Trumbull et al. | 239/142 |
| 3,058,632 | 10/1962 | Stremmel et al. | 222/567 |
| 3,112,743 | 12/1963 | Cochran et al. | 128/92 |
| 3,141,583 | 7/1964 | Mapel et al. | 222/309 |
| 3,160,156 | 12/1964 | Tyler | 128/236 |
| 3,193,146 | 7/1965 | Isgriggs et al. | 222/82 |
| 3,255,747 | 6/1966 | Cochran et al. | 128/92 |
| 3,368,592 | 2/1968 | Thiel et al. | 141/69 |
| 3,815,878 | 6/1974 | Baskas et al. | 259/37 |
| 3,894,663 | 7/1975 | Carhart et al. | 222/309 |
| 4,090,639 | 5/1978 | Campbell et al. | 222/43 |
| 4,338,925 | 7/1982 | Miller | 128/92 E |
| 4,339,058 | 7/1982 | Wendt | 222/309 |
| 4,342,310 | 8/1982 | Lindmayer et al. | 128/207.25 |
| 4,356,938 | 11/1982 | Kayser | 222/327 |
| 4,364,388 | 12/1982 | Cech | 128/234 |
| 4,406,654 | 9/1983 | Bristow | 604/209 |
| 4,425,121 | 1/1984 | Young et al. | 604/209 |
| 4,546,767 | 10/1985 | Smith | 128/92 E |
| 4,569,662 | 2/1986 | Dragan | 433/89 |
| 4,576,152 | 3/1986 | Müller et al. | 128/92 R |
| 4,619,613 | 10/1986 | Dragan | 433/90 |
| 4,671,263 | 6/1987 | Draenert | 128/92 VO |
| 4,738,664 | 4/1988 | Prindle | 604/228 |
| 4,768,955 | 9/1988 | Hirdes | 433/89 |

(List continued on next page.)

*Primary Examiner*—Kenneth Bomberg
*Attorney, Agent, or Firm*—Cary R. Reeves

[57] ABSTRACT

A paste injector gun, especially adapted for injecting bone cement, has first and second mechanical advantages. In a first embodiment, the first and second mechanical advantages are produced by two fulcrums engageable during different portions of the trigger stroke. In a second embodiment, the first and second mechanical advantages are produced by a fixed fulcrum and a rotatable fulcrum. The first mechanical advantage is greater than the second such that the first facilitates pressurizing the bone cement and the second facilitates high volume dispensing of the bone cement. The injector gun also includes a pair of U-shaped slots. One of the slots is sized to accept a large cement cartridge and the other slot is sized to accept a small cement cartridge. An alternative embodiment provides a hinged cartridge retaining gate for closing the U-shaped slots for positive retention of the cartridge.

16 Claims, 9 Drawing Sheets

OTHER PUBLICATIONS

| | | | |
|---|---|---|---|
| 4,787,893 | 11/1988 | Vilette | 604/188 |
| 4,840,294 | 6/1989 | Ernst | 222/391 X |
| 4,966,601 | 10/1990 | Draenert | 606/92 |
| 4,973,334 | 11/1990 | Ziemann | 606/92 |
| 4,994,065 | 2/1991 | Gibbs et al. | 606/92 |
| 5,022,563 | 6/1991 | Marchitto et al. | 222/391 X |
| 5,052,243 | 10/1991 | Tepic | 74/523 |
| 5,125,836 | 6/1992 | Dragan et al. | 433/90 |
| 5,197,635 | 3/1993 | Chang | 222/137 |
| 5,215,230 | 6/1993 | Lee | 222/391 X |
| 5,304,147 | 4/1994 | Johnson et al. | 604/183 |
| 5,336,014 | 8/1994 | Keller | 222/327 X |
| 5,381,931 | 1/1995 | Chang | 222/309 |
| 5,390,831 | 2/1995 | Schneider | 222/391 |
| 5,431,654 | 7/1995 | Nic | 606/92 |
| 5,615,807 | 4/1997 | Peng | 222/391 |
| 5,638,997 | 6/1997 | Hawkins et al. | 222/391 |
| 5,704,518 | 1/1998 | Vanmoor | 222/327 |
| 5,755,362 | 5/1998 | Rodriguez, Jr. et al. | 222/391 |

BONE CEMENT INJECTOR GUN

CROSS-REFERENCE TO RELATED APPLICATION

This application is a continuation-in-part of application Ser. No. 08/529,814 filed Sep. 18, 1995, U.S. Pat. No. 5,638,997.

BACKGROUND OF THE INVENTION

The present invention relates to injector guns for dispensing pastes, and more particularly, to injector guns that can dispense paste from a cartridge both at low pressure and high volume for filling a void and at high pressure and low volume for pressurizing the paste in the void. The present invention further includes means for connecting the injector gun to cartridges having different diameters.

Prior art injector guns have a trigger mechanism that includes a trigger in the form of a lever. The trigger includes an input end, an output end and a fulcrum between the ends. When the input end is squeezed by the user, the trigger pivots about the fulcrum causing the output end to move. The mechanical advantage of an injector gun is the amount the force applied to the input end is multiplied at the output end and can be calculated as the ratio of the length of the trigger from the fulcrum to the input end over the length of the trigger from the fulcrum to the output end. A high mechanical advantage multiplies the force more but generates less motion at the output end than does a low mechanical advantage. Therefore, a high mechanical advantage facilitates generating a high pressure in the paste but extrudes a low volume of paste whereas a low mechanical advantage generates a low pressure in the paste but extrudes a high volume of paste.

A typical application for paste injector guns is for dispensing bone cement from a cartridge into the intramedullary canal of the femur. Miller discloses such an injector gun in U.S. Pat. 4,338,925. Miller teaches the advantage of improved implant fixation that results from pressurizing the cement after filling the canal in order to force the cement into bony interstices. Therefore, Miller requires an injector gun with a relatively high mechanical advantage. However, as is typical of most injector guns, Miller's injector gun utilizes a trigger mechanism with a constant mechanical advantage that is a compromise between a low mechanical advantage that delivers a high flow rate for rapid filling and a high mechanical advantage that delivers high pressure for pressurizing the cement. To increase the flow of cement, the surgeon must squeeze the trigger faster. To increase the pressure on the cement, the surgeon must squeeze the trigger harder.

Some investigators have provided injector guns with user adjustable mechanical advantages. In U.S. Pat. No. 5,197,635, Chang teaches a mechanism that includes a bearing element that is adjustable up and down on the trigger and held in place by a set screw. By moving the bearing element, the output length of the trigger is changed and thus the mechanical advantage is changed. In U.S. Pat. No. 5,381,931, Chang teaches a different mechanism for selectively lengthening the output length of the trigger comprising an eccentric rotatable element attached to the output end of the trigger. In U.S. Pat. No. 5,431,654, Nic teaches another mechanism for changing mechanical advantage. The upper end of a trigger 70 includes an enlarged head 74 which carries a low force/large displacement drive pawl 80 and a high force/low displacement drive pawl 81. The pawls are biased by springs 86 and 87 into engagement with teeth 54 on rod 50. When both pawls are in contact with the rod 50, the low force pawl 80 controls the advancement of the rod 50 because of its longer travel. If high force/low displacement rod advancement is desired, switch lever 92 is moved downwardly which causes it to contact push-down pin 94 which in turn moves low force pawl 80 out of engagement with the teeth 54 as shown in FIG. 5.

A disadvantage of prior art injector guns with user adjustable mechanical advantages is the need for additional parts and the resulting complexity in the trigger mechanism. A further disadvantage of prior art cement injector guns is that they are configured to connect only to a cement cartridge having a single specified diameter. These prior art cement injector guns are therefore incapable of dispensing cement from differently sized cartridges such as from different manufacturers or different styles or sizes from the same manufacturer.

SUMMARY OF THE INVENTION

The present invention solves these problems of the prior art by providing in a first embodiment a paste injector gun, especially adapted for injecting bone cement, having first and second mechanical advantages corresponding to different portions of the trigger stroke. The first mechanical advantage is greater than the second such that the first facilitates pressurizing the bone cement and the second facilitates high volume dispensing of the bone cement.

The two mechanical advantages are accomplished by providing a trigger mechanism with a trigger lever pivotably connected to a drive plate at the output end. The trigger mechanism includes two fulcrums which provide two sequential centers of rotation. In the initial position, the first fulcrum is engaged. As the trigger is squeezed, a high mechanical advantage enables cement pressurization because the first fulcrum is close to the output end of the trigger lever. At the end of this first stage of trigger travel, the second fulcrum is engaged. During the second stage of trigger travel, the trigger lever pivots about the second fulcrum. This results in a higher flow volume because the second pivot point is further from the output end of the trigger lever. With the present invention there are no screws or switches which must be adjusted to change mechanical advantage. The two mechanical advantages are designed into each squeeze of the trigger. The first portion of the trigger stroke produces high pressure and the second portion of the trigger stroke produces high flow volume. If high flow is desired, full strokes are used. If high pressure is desired, short strokes are used.

The present invention also includes a second embodiment having a pair of fulcrums mounted on the handle opposite the trigger. One of the fulcrums is rotatable between a first position in which it is engageable with the trigger and a second position in which it is not engageable with the trigger. A knob connected to the rotatable fulcrum extends from the housing and facilitates moving the rotatable fulcrum between the first and second positions. When the rotatable fulcrum is in the first, engaging position the rotatable fulcrum engages the trigger and provides a relatively low mechanical advantage and high fill rate. When the rotatable fulcrum is in the second, nonengaging position the fixed fulcrum is engageable with the trigger and provides a relatively high mechanical advantage and high pressure. This embodiment remains simple, requiring only the addition of a rotatable fulcrum and knob, yet provides the option of two mechanical advantages each of which is useable over the entire range of trigger travel.

The injector gun of the present invention also includes a pair of U-shaped slots for gripping a bone cement containing cartridge. One of the slots is sized to accept a large cement cartridge. The other slot is sized to accept a small cement cartridge. One embodiment includes a hinged cartridge retention gate that closes the U-shaped slot for positive retention of the cartridge.

DETAILED DESCRIPTION OF THE INVENTION

Figure 1:
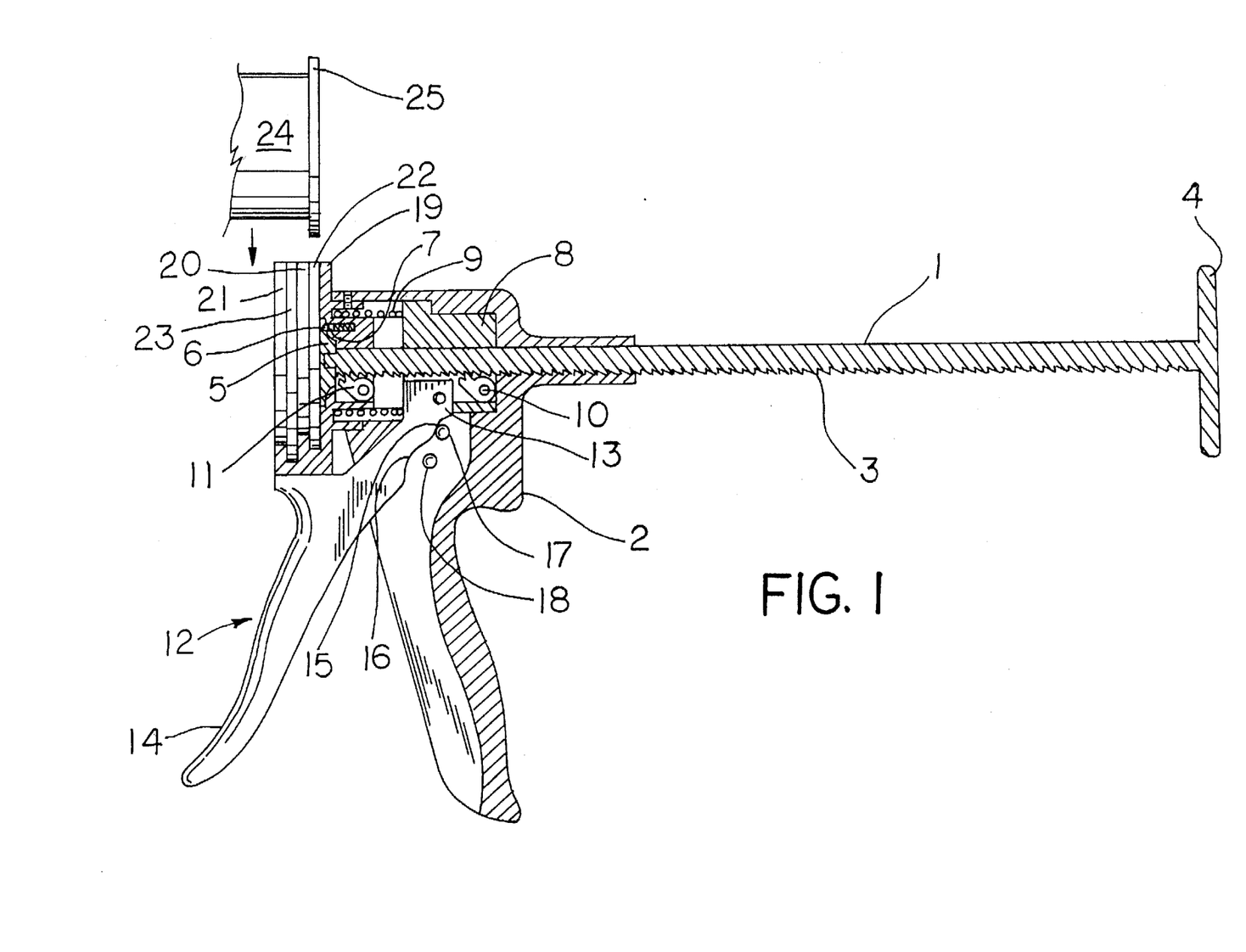
FIG. 1 is a side cross-sectional view of the cement injector gun of the present invention.
Figure 2:
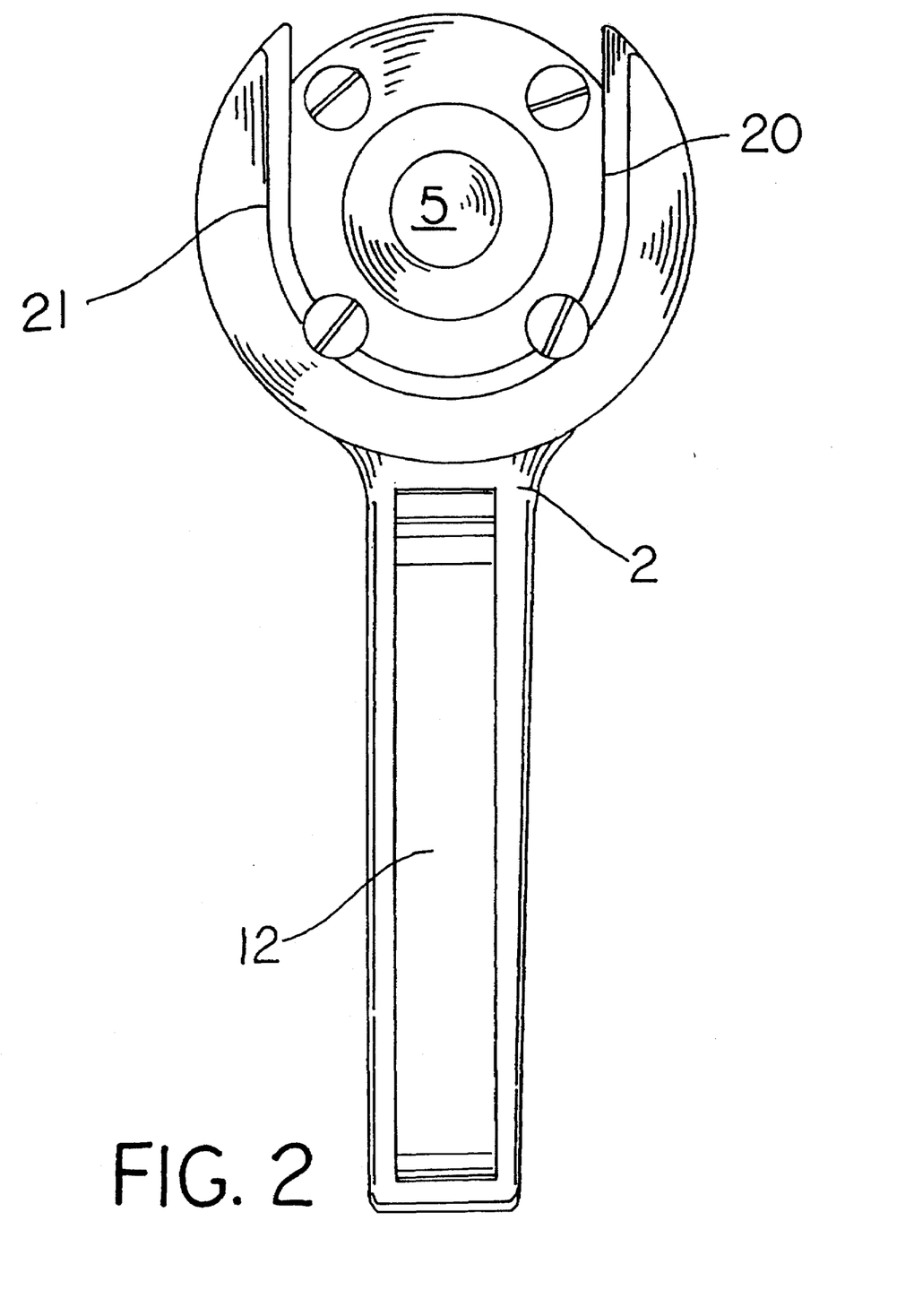
FIG. 2 is an end view of the cement injector gun of FIG. 1.
Figure 3:
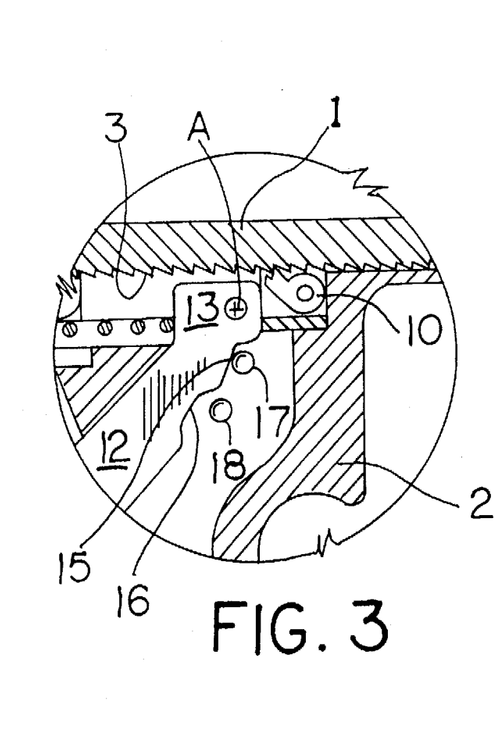
FIGS. 3–5 are side cross-sectional views of the trigger mechanism of the cement injector gun of FIG. 1 showing the operation of the trigger.

FIGS. 1 and 2 depict a cement injector gun according to the present invention.

A shaft 1 is mounted for axial translation within a housing 2. The shaft includes teeth 3 formed on a portion of its circumference and along its length. A handle 4 is attached to one end of the shaft 1 and a shaft plate 5 is attached to the other end of the shaft 1. The shaft plate 5 contains a recess 6 in its back side. A spring loaded plunger 7 is mounted in the housing behind the shaft plate 5 such that when the teeth 3 are oriented downwardly, the plunger 7 is aligned with the recess 6. A drive plate 8 is mounted for axial translation within the housing 2 and is coaxial with and surrounds the shaft 1. A return spring 9 biases the drive plate 8 rearwardly in the housing. The drive plate 8 carries a drive ratchet 10 rotatably mounted on the drive plate 8. A spring biases the drive ratchet 10 into contact with the shaft 1 such that the drive ratchet 10 will engage the teeth 3 when they are oriented downwardly. A retaining ratchet 11 is rotatably mounted on the housing 2 and it is also spring biased into contact with the shaft 1 such that the retaining ratchet 11 will engage the teeth 3 when they are oriented downwardly. The injector gun includes a trigger having a trigger lever 12 pivotally attached to the drive plate 8 at the trigger lever's output end 13. The input end 14 of the trigger lever 12 extends from the housing 2. The trigger lever 12 also includes first and second bearing portions 15 and 16. First and second fulcrums, 17 and 18, are attached to the housing 2 in alignment with the first and second bearing portions 15 and 16. In the embodiment shown in FIG. 1, the fulcrums are in the form of cylindrical pins attached to the housing and the bearing portions are in the form of scalloped regions formed on the trigger. A cartridge adapter 19 is mounted on the front of the housing 2. The cartridge adapter 19 contains first and second U-shaped slots, 20 and 21, lying on a common axis in axial alignment with the shaft 1. The U-shaped slots lie in parallel planes to one another. The second U-shaped slot 21 has a larger radius than the first U-shaped slot 20. The U-shaped slots are shaped to engage a cartridge 24 having a rim 25. Each U-shaped slot includes a peripheral groove 22 and 23 to engage the rim 25 to prevent the cartridge from moving forward as the shaft presses against the cartridge. The first U-shaped slot is at least 10% narrower, preferably at least 20% narrower than the second slot. Therefore, first U-shaped slot 20 is sized for a small cartridge and the second U-shaped slot 21 is sized for a large cartridge. The first U-shaped slot 20 is positioned on the common axis nearer to the trigger mechanism than the second U-shaped slot 21 such that a cartridge 24 engaged with the first U-shaped slot 20 will extend through the second U-shaped slot 21 and a cartridge engaged with the second U-shaped slot 21 will not extend through the first U-shaped slot 20.

Referring now to FIGS. 1–5, the function of the cement injector gun will be explained. In use the handle 4 is turned until the teeth 3 disengage the ratchets 10 and 11.

The shaft 1 is then pulled backward until the plunger 7 is depressed and the shaft plate 5 is fully seated in the housing 2. The handle 4 is then rotated until the teeth 3 are in alignment with the ratchets 10 and 11. As the teeth 3 come into alignment with the ratchets 10 and 11, the recess 6 will come into alignment with the plunger 7 and the plunger 7 will pop out to extend into the recess 6. The popping of the plunger 7 into the recess 6 is thus an audible and tactile indicator of proper tooth-to-ratchet alignment. With the shaft 1 fully retracted, a cartridge 24 is slid into the appropriate slot, 20 or 21, of the cartridge adapter 19.

To dispense cement, the trigger is squeezed by applying pressure to the input end 14 of the trigger lever 12. The trigger has a range of rotation from the rest position shown in FIG. 3 to the stop position shown in FIG. 5. In the preferred embodiment, the range of rotation is divided into two stages. The first stage is from the initial rest position to an intermediate position where the center of rotation changes from the first fulcrum to the second fulcrum. The second stage is from this intermediate position to the stop position. During the first stage, the first bearing portion 15 contacts the first fulcrum 17 providing a first center of rotation. The trigger lever 12 pivots about the first fulcrum 17 causing the drive plate 8 and drive ratchet 10 to move forward. The drive ratchet 10 presses against the teeth 3 thus driving the shaft 1 forward as well. As the shaft moves forward, the retaining ratchet 11 pivots against its biasing spring and allows the teeth 3 to slip by it. The forward moving shaft plate 5 engages the cartridge 24 and forces cement from it.

Figure 4:
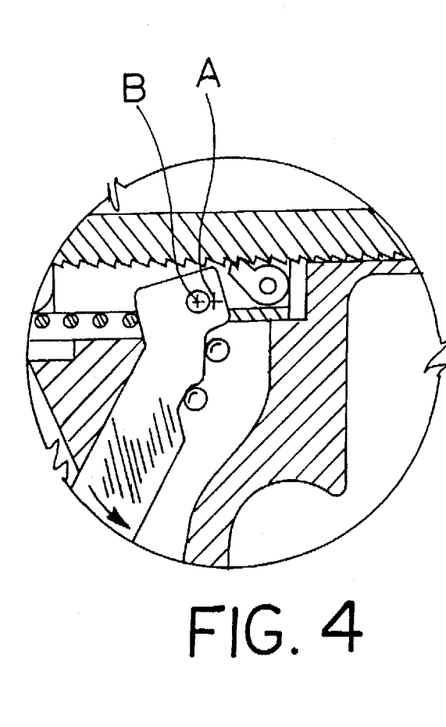

Because the first fulcrum 17 is near the output end 13, the first mechanical advantage is relatively high and a small input force yields a large output force for driving the shaft forward. This high mechanical advantage allows a large amount of pressure to be generated in the cement to force cement into bony interstices. Corresponding to the high mechanical advantage is a small movement of the shaft equal to the distance between points A and B as shown in FIG. 4. This small shaft 1 movement dispenses a relatively low volume of cement. Preferably, the trigger lever 12 rotates about the first fulcrum 17 during the first 15° of trigger travel at which point it contacts the second fulcrum 18. During this first stage of trigger travel, corresponding to rotation about the first fulcrum 17, the shaft 1 preferably travels forward 2 teeth or a distance of about 0.1". The distance the shaft moves for each degree of trigger rotation about the first fulcrum is the first advancement rate.

Figure 5:
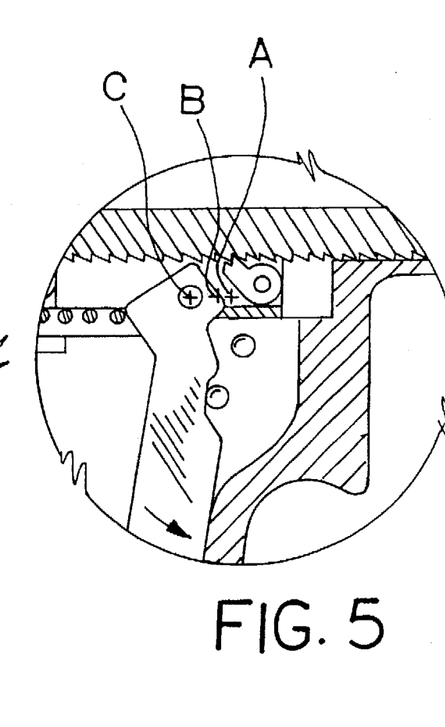

During the second stage of trigger travel, the trigger lever 12 rotates about a second center of rotation provided by the second fulcrum 18 as shown in FIG. 5. Because the second fulcrum 18 is further from the output end 13, the second mechanical advantage is relatively low. Preferably, the second mechanical advantage is from 10% to 90% of the first mechanical advantage, more preferably 25% to 50%. Corresponding to this low mechanical advantage is a relatively large shaft movement corresponding to the distance between the points B and C. This large shaft movement dispenses a large volume of cement but less pressure can be generated in the cement from a particular input force because of the lower mechanical advantage. Preferably this second stage of trigger travel corresponds to approximately 20° of trigger lever 12 rotation and moves the shaft forward 6 teeth or a distance of about 0.31. The distance the shaft moves for each degree of trigger rotation about the second fulcrum is the second advancement rate. Preferably the second advancement rate is 1.1 to 10 times the first advancement rate, more preferably 2 to 4 times.

Thus two mechanical advantages are designed into each squeeze of the trigger. The first portion of the trigger stroke produces high pressure and the second portion of the trigger stroke produces high flow volume. If high flow is desired, full strokes are used. If high pressure is desired, short strokes are used. For a typical surgical procedure, full strokes would be used to fill a bone canal. Once the canal is filled, short strokes would be used to build fluid pressure in the cement in the bone canal.

Figure 6:
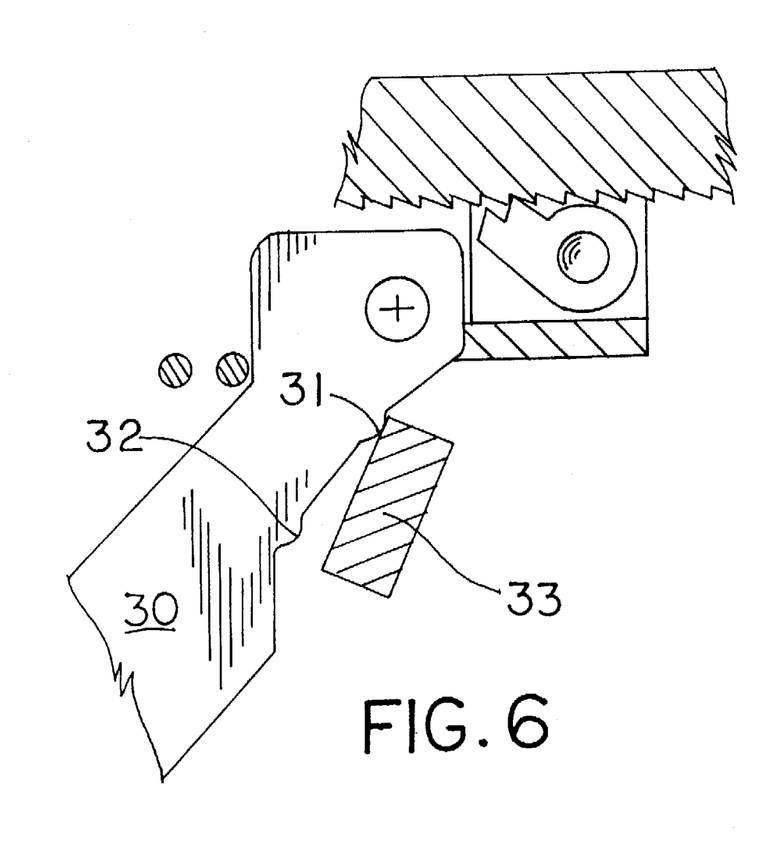
FIG. 6 is a side cross-sectional view of an alternative embodiment of the trigger mechanism of the cement injector gun of the present invention.
Figure 7:
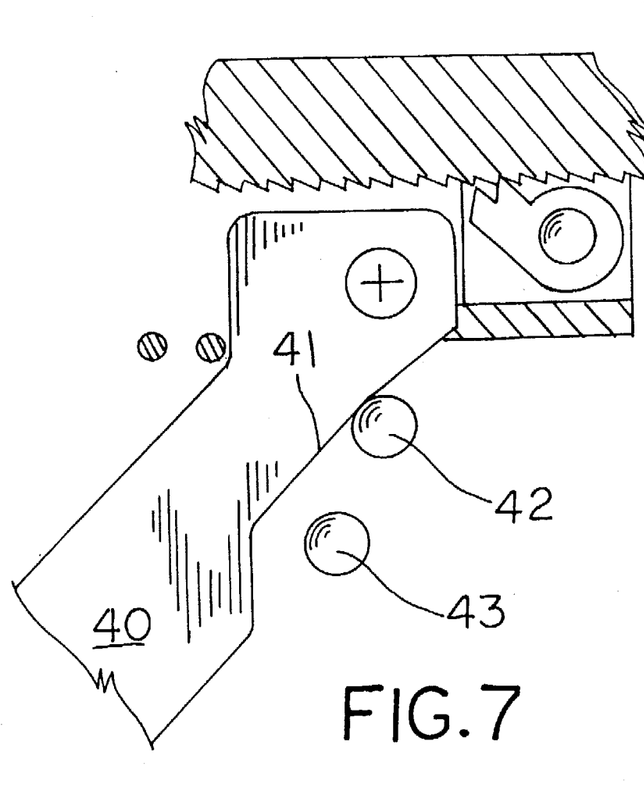
FIG. 7 is a side cross-sectional view of another alternative embodiment of the trigger mechanism of the cement injector gun of the present invention.
Figures 8, 9:
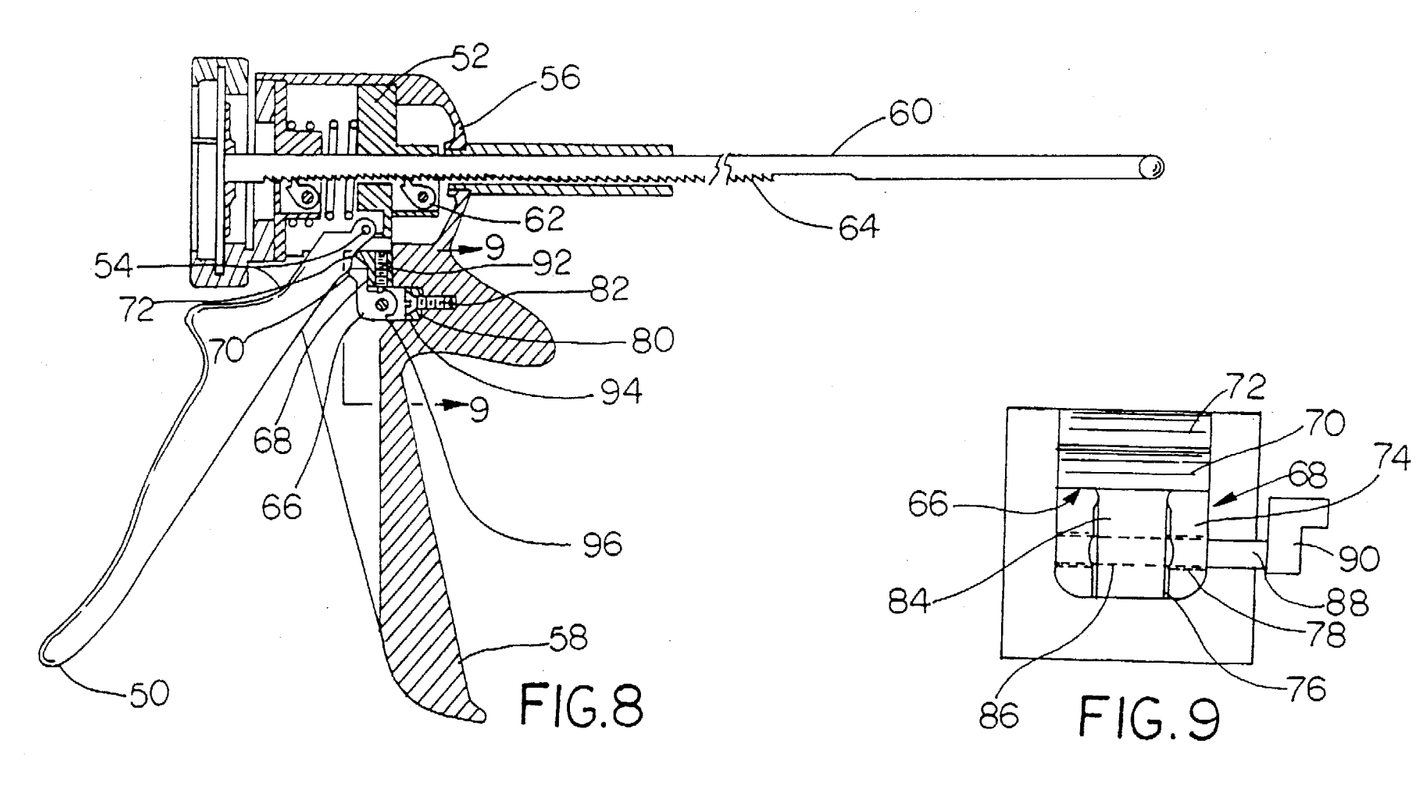
FIG. 8 is a side cross-sectional view of an alternative embodiment of the cement injector gun of the present invention.
FIG. 9 is a partial front view of the cement gun of FIG. 8 showing the two fulcrums.

FIGS. 6 and 7 depict alternative embodiments of the present invention. In FIG. 6, a trigger lever 30 includes two fulcrums 31 and 32 in the form of raised areas or bumps. A bearing member 33 is attached to the housing opposite the fulcrums 31 and 32. As the trigger lever 30 is squeezed, the first fulcrum 31 initially contacts the bearing member 33 and the trigger lever 30 rotates about the first fulcrum 31 during the first stage of trigger travel. During the second stage of trigger travel, the trigger lever 30 rotates about the second fulcrum 32. In FIG. 7, a trigger lever 40 includes a flat bearing portion 41. Two fulcrums 42 and 43, similar to those depicted in FIG. 1, are attached to the housing opposite the bearing portion 41. As the trigger lever 40 is squeezed, the bearing portion 41 initially contacts the first fulcrum 42 and the trigger lever 40 rotates about the first fulcrum 42 during the first stage of trigger travel. During the second stage of trigger travel, the trigger lever 40 rotates about the second fulcrum 43. The embodiments of FIGS. 6 and 7 provide the same function as the embodiment of FIG. 1. They provide a cement injector gun having a trigger mechanism with two stages of travel provided by two fulcrums that are engaged sequentially during the trigger stroke. The first stage is characterized by a high mechanical advantage for pressurizing the bone cement and the second stage is characterized by a low mechanical advantage for extruding a large volume of bone cement. The embodiments of FIGS. 6 and 7 differ from that of FIG. 1 only in the shape and placement of the fulcrums.

Figures 10, 11:
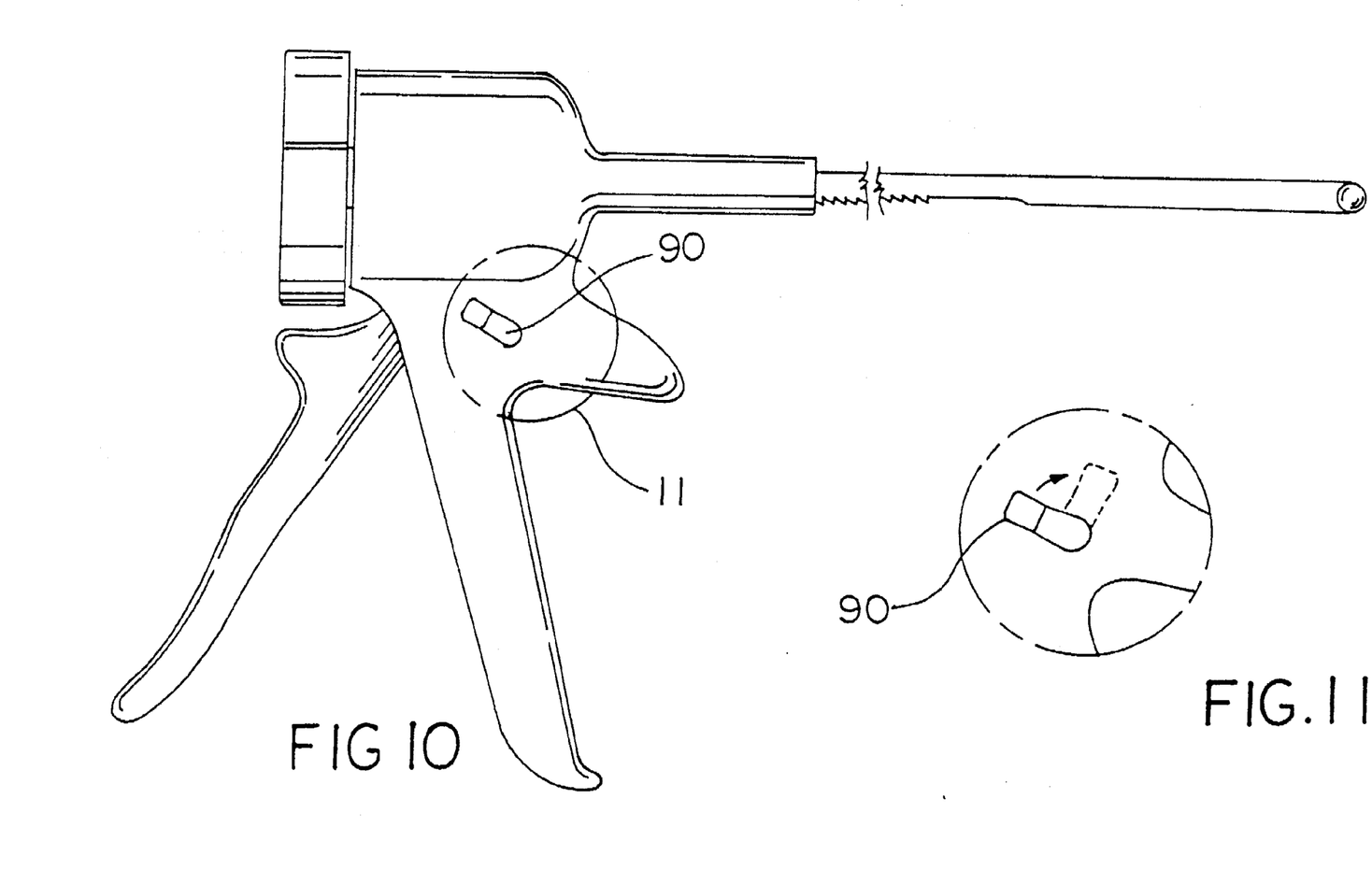
FIG. 10 is a side view of the cement injector gun of FIG. 8.
FIG. 11 is a side detail view of the cement gun of FIG. 8 showing the two knob positions.
Figure 12:
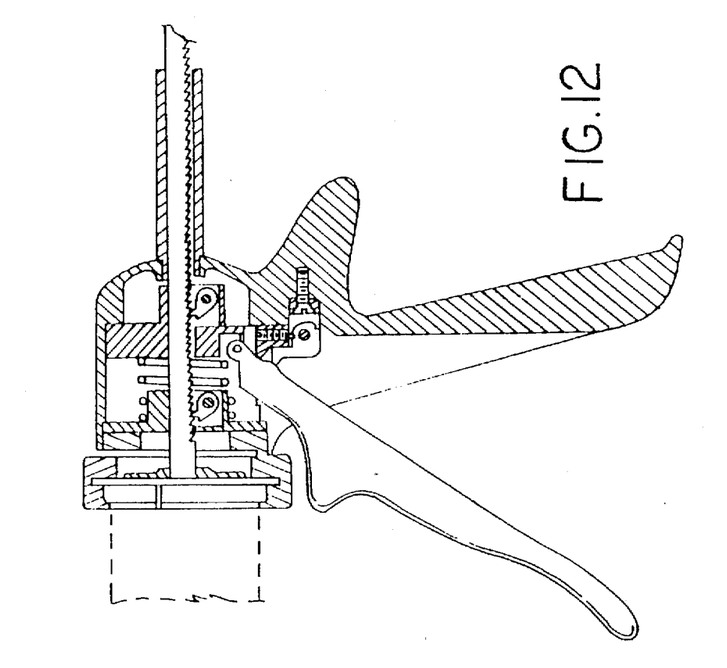
FIGS. 12–13 are side cross-sectional views of the cement injector gun of FIG. 8 showing the trigger actuation with the rotatable fulcrum in a first position.
Figure 13:
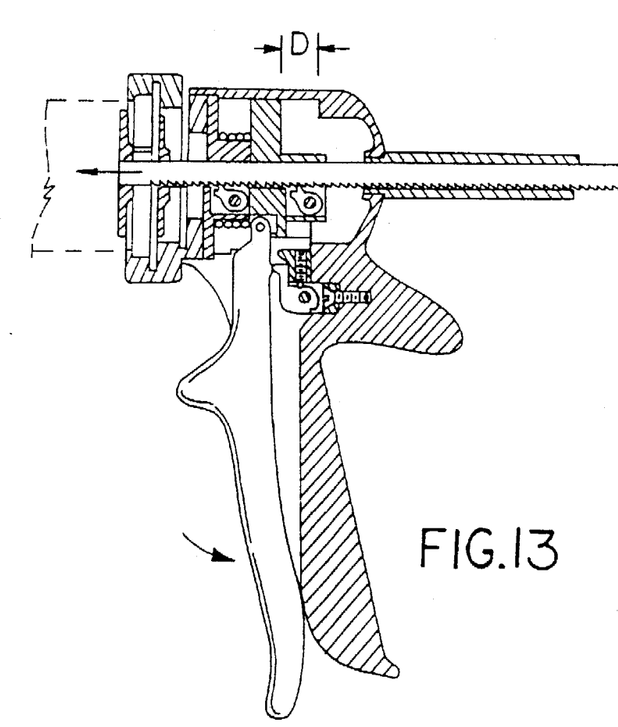
Figure 14:
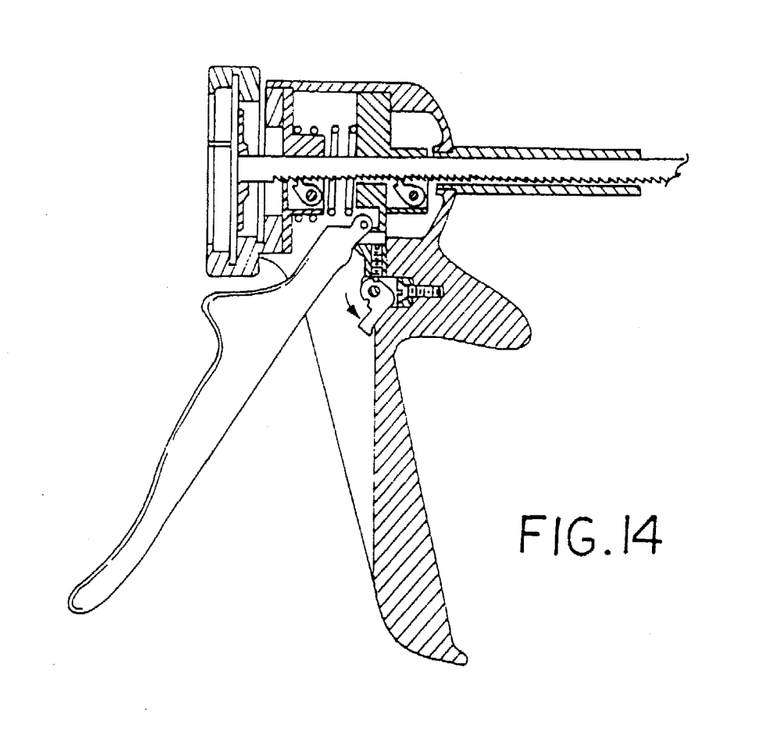
FIGS. 14–15 are side cross-sectional views of the cement injector gun of FIG. 8 showing the trigger actuation with the rotatable fulcrum in a second position.
Figure 15:
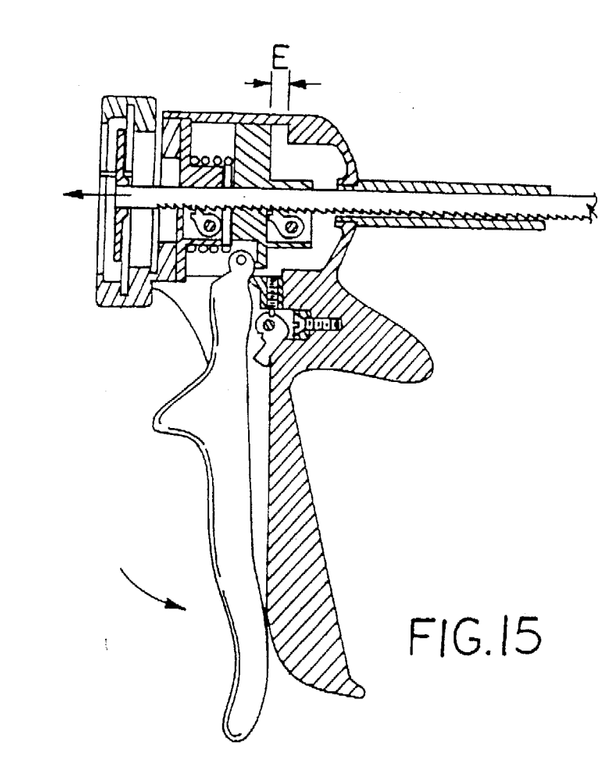

Another alternative embodiment of the present invention is shown in FIGS. 8–17. This rotatable fulcrum embodiment includes a trigger 50 attached to a drive plate 52 at a pivot point 54. The trigger and drive plate assembly is mounted for axial displacement in a housing 56 having an integral downwardly extending handle 58. A toothed shaft 60 is also mounted for axial translation in the housing and extends through the drive plate 52. The drive plate 52 carries a drive ratchet 62 which engages the shaft teeth 64. A pair of fulcrums 66 and 68, having bearing portions 70 and 72, are mounted on the handle 58 opposite the trigger 50. One of the fulcrums 66 is rotatable between a first position in which it is engageable with the 50 trigger, as shown in FIGS. 8–13, and a second position in which it is not engageable with the trigger, as shown in FIGS. 11, 14 and 15. Another fulcrum 68 is fixed and has a lower body portion 74 including a slot 76 and cross hole 78 perpendicular to the slot. The fixed fulcrum also includes a rearwardly facing mounting hole 80. The fixed fulcrum 66 is held in place by a screw 82 which extends through the hole 80 and into the handle 58. The rotatable fulcrum 66 has a lower pivot portion 84 having a transverse hole 86. The lower pivot portion 84 is mounted in the slot 76 for rotation. A pin 88 extends through the cross hole 78 and transverse hole 86. A knob 90 is mounted on the end of the pin 88. The pin 88 is fixed relative to the rotatable fulcrum 66 and the knob 90 such as by press fitting or soldering. The pin 88 is free to rotate in the cross hole 78. Thus the rotatable fulcrum 66 rotates with the knob 90 when the knob is actuated. A spring loaded ball detent 92 is mounted in the fixed fulcrum 68 such that its ball is biased against the lower pivot portion 84 of the rotatable fulcrum 66. Notches 94 and 96 in the lower pivot portion 84 are located to receive the ball when the rotatable fulcrum is in the first and second positions respectively. The ball detent 92 and notch 94 and 96 engagement helps to maintain the rotatable fulcrum 96 in the first and second positions. Turning the knob 90 with sufficient force overcomes the ball detent 92 and notch 94 and 96 engagement and allows the rotatable fulcrum to be moved between the first and second positions.

Alternative arrangements of the trigger-to-fulcrum bearing relationship are encompassed within this invention. For example, the fulcrums and rotating knob can be mounted on the trigger and bear against the housing.

In use, the rotatable fulcrum 66 is moved into the first position so that it is engageable with the trigger. The trigger 50 is squeezed causing it to pivot around the pivot point 54. With the trigger in contact with the rotatable fulcrum, an instant center of rotation is established between the trigger 50 and the fulcrum 66 at the contact point. As the trigger 50 pivots, this instant center moves around the surface of the bearing portion 70 of the fulcrum and the drive plate 52 is levered forward in the housing. The drive plate in turn engages the shaft 60 via the drive ratchet 62 and drives the shaft 60 forward to dispense cement from a cement cartridge. The distance from the pivot point 54 on the drive plate to the instant center of rotation is relatively long when the rotatable fulcrum 66 is in engagement with the trigger and therefore the output end of the trigger lever is relatively long and thus mechanical advantage of the trigger mechanism is relatively low. This results in a particular actuation force yielding a relatively high volume and low pressure cement flow. This motion is depicted in FIGS. 12 and 13. As the trigger 50 moves through its range of travel, the drive plate 52 and consequently the shaft 60 move forward the distance "D".

When higher pressure is desired, such as for pressurizing cement in the intramedullary canal, the rotatable fulcrum 66 is placed in its second position so that it is not engageable with the trigger 50. Thus, when the trigger 50 is actuated, it comes to bear on the fixed fulcrum 68 which is located nearer to the drive plate 52 than the rotatable fulcrum 66 is when it engages the trigger 50. The instant centers of rotation between the trigger 50 and the fixed fulcrum 68 are closer to the pivot point 54 on the drive plate and thus the output end of the trigger lever is relatively short compared to when the rotatable fulcrum is used. Thus the mechanical advantage is relatively high and the particular actuation force will yield a relatively low volume and high pressure cement flow. This motion is depicted in FIGS. 14 and 15. As the trigger 50 moves through its range of travel, the drive plate 52 and consequently the shaft 60 move forward the distance "E". The distance "E", produced with the fixed fulcrum, is less than the distance "D", produced with the rotatable fulcrum.

Figures 16, 17, 18:
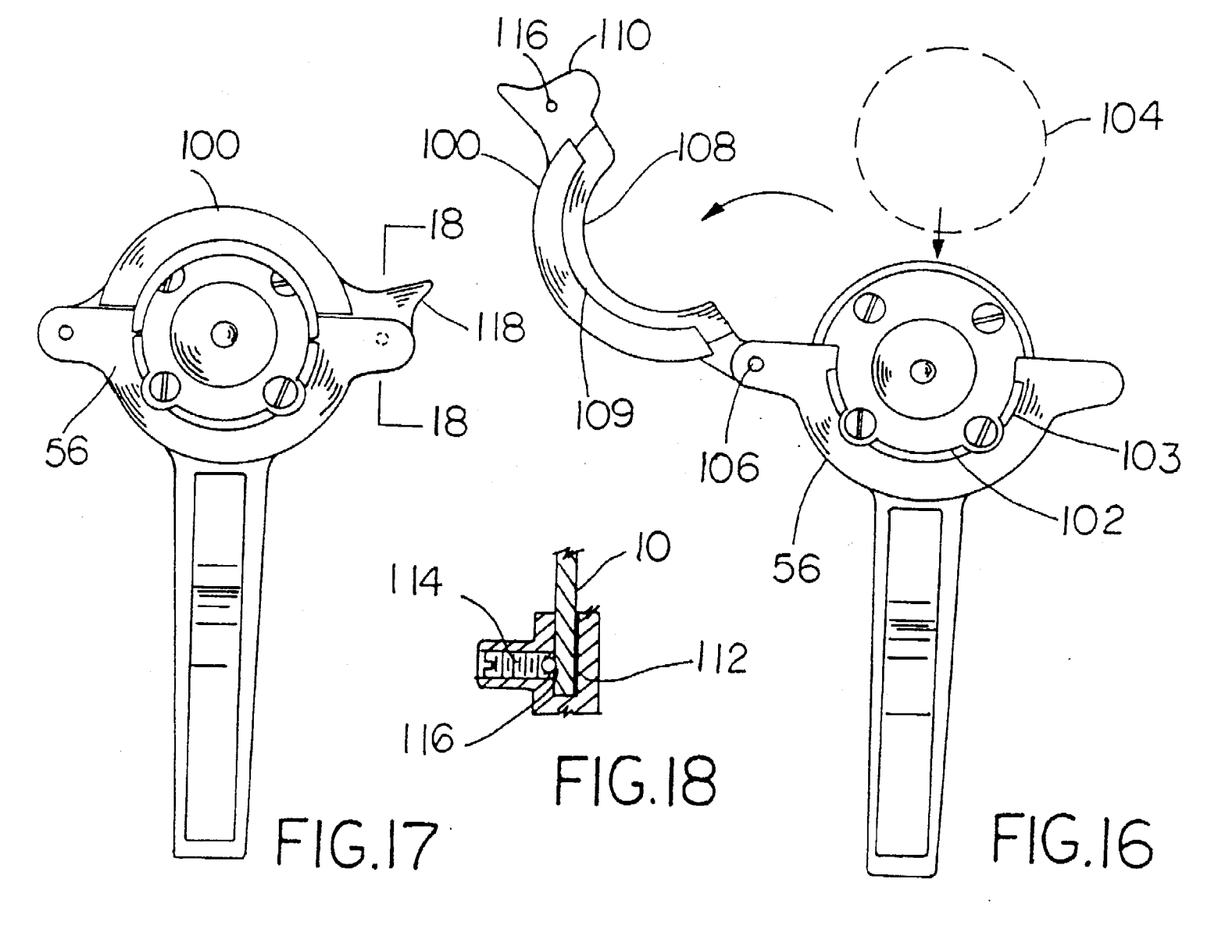
FIG. 16 is a front view of the cement injector gun of FIG. 8 showing the hinged cartridge retention gate in the open position.
FIG. 17 is a front view of the cement injector gun of FIG. 8 showing the hinged cartridge retention gate in the closed position.
FIG. 18 is a cross-sectional view of the cement injector gun of FIG. 16 showing the locking mechanism of the hinged cartridge retention gate.

FIGS. 16–18 show an alternative hinged cartridge retention gate 100 that closes the U-shaped slots 102 and 103 for positive retention of the cartridge 104. The gate is hinged 106 to the housing 56 on one side. This allows the gate 100 to be swung open so that a cartridge 104 can be slid into the U-shaped slot 102 or 103. The gate 100 is then swung closed to close the U-shaped slots 102 and 103 and positively retain the cement cartridge 104. The gate 100 has slots 108 and 109 corresponding to slots 102 and 103 for retaining small and large cartridges respectively. The gate 100 includes a closure tab 110 on the side opposite the hinge 106. The housing 56 includes a closure tab receiver slot 112 formed in the housing opposite the hinge 106. When the gate 100 is closed, the closure tab 110 is received by the closure tab receiver slot 112. A spring loaded ball detent 114 is mounted adjacent the receiver slot 112 with its ball projecting into the slot. A depression 116 formed in the closure tab 110 receives the ball of the ball detent 114 to positively maintain the gate in the closed position. An ear 118 projects from the closure tab 110. The ear 118 allows a user to apply an upward force on the closure tab 110 sufficient to overcome the engagement between the ball detent 114 and the depression 116 and open the gate.

Other alternatives in the construction and use of the paste injector gun will come to mind to those skilled in the art. For example, additional trigger stages or rotatable fulcrums, each with its own mechanical advantage, could be incorporated so that there would be more than two stages. By doing this, the change in mechanical advantage could be made more gradual. Also, the benefits of the paste injector gun of this invention can be used advantageously for dispensing pastes other than bone cement. Finally, it will be understood by those skilled in the art that further variations in design and construction may be made to the preferred embodiment without departing from the spirit and scope of the invention defined by the appended claims.

What is claimed is:

1. A paste injector gun comprising:

a housing having a longitudinal axis;

a drive plate mounted in the housing for translation along the longitudinal axis;

a shaft mounted in the housing for translation along the longitudinal axis, the shaft passing through the drive plate;

a trigger pivotably attached to the drive plate at a pivot point and extending from the drive plate;

a first fulcrum mounted on the housing opposite the trigger such that when the trigger pivots about the pivot point the trigger contacts and rotates about the fulcrum and the drive plate is moved along the axis carrying the shaft with it; and a second fulcrum, the second fulcrum being mounted for rotation on the housing opposite the trigger, the second fulcrum being rotatable between a first position in which it is not engageable with the trigger and a second position in which it is engageable with the trigger.

2. The paste injector gun of claim 1 wherein the first fulcrum corresponds to a first mechanical advantage and the second fulcrum corresponds to a second mechanical advantage, the first and second mechanical advantages being different, the trigger engaging the first fulcrum to produce the first mechanical advantage when the second fulcrum is in the first position and the trigger engaging the second fulcrum to produce the second mechanical advantage when the second fulcrum is in the second position.

3. The paste injector gun of claim 2 further including a spring loaded detent adjacent the second fulcrum, the second fulcrum further including a first notch corresponding to the first position and a second notch corresponding to the second position, the detent engaging the first notch when the second fulcrum is in the first position and the second notch when the second fulcrum is in the second position.

4. The paste injector gun of claim 1 wherein the housing further includes a U-shaped opening for receiving a cartridge and the paste injector gun further includes a gate hinged at one end to the housing, the gate rotatable between an open position in which a cartridge can be positioned in the U-shaped opening and a closed position in which the gate closes the U-shaped opening for positive retention of the cartridge.

5. The paste injector gun of claim 4 wherein the gate further includes a closure tab extending from an end opposite the hinged end and the housing includes a tab receiving slot, the closure tab fitting into the tab receiving slot when the gate is in the closed position.

6. A paste injector gun comprising:

a housing having a longitudinal axis;

a drive plate mounted in the housing for translation along the longitudinal axis;

a shaft mounted in the housing for translation along the longitudinal axis, the shaft passing through the drive plate;

a trigger pivotably attached to the drive plate at a pivot point and extending from the drive plate; and a first fulcrum mounted on the housing opposite the trigger such that when the trigger pivots about the pivot point the trigger contacts and rotates about the fulcrum and the drive plate is moved along the axis carrying the shaft with it, the housing further including a U-shaped opening for receiving a cartridge and the paste injector gun further includes a gate hinged at one end to the housing, the gate rotatable between an open position in which a cartridge can be positioned in the U-shaped opening and a closed position in which the gate closes the U-shaped opening for positive retention of the cartridge, the gate further including a closure tab extending from an end opposite the hinged end and the housing includes a tab receiving slot, the closure tab fitting into the tab receiving slot when the gate is in the closed position and a spring loaded detent is mounted adjacent the tab receiving slot and projects into the tab receiving slot, the closure tab including a depression for receiving the detent when the gate is in the closed position.

7. The paste injector gun of claim 6 wherein the closure tab includes an outwardly extending ear, the ear being shaped to facilitate gripping the gate by a user.

8. The paste injector gun of claim 4 wherein the housing includes first and second U-shaped slots adjacent the U-shaped opening and the gate includes corresponding first and second U-shaped slots aligned with the first and second U-shaped slots in the housing, the first slots being sized to accept a small diameter cement cartridge and the second slots being sized to accept a large diameter cement cartridge.

9. A paste injector gun comprising:

a trigger;

first pivot means for providing a first center of rotation for the trigger, the first pivot means corresponding to a first mechanical advantage; and second pivot means for providing a second center of rotation for the trigger, the second pivot means corresponding to a second mechanical advantage, the second pivot means being rotatable between a first position in which it is not engageable with the trigger and a second position in which it is engageable with the trigger.

10. The paste injector gun of claim 9 wherein the first pivot means comprises a first fulcrum and the second pivot means comprises a second fulcrum.

11. The paste injector gun of claim 10 wherein the first fulcrum corresponds to the first mechanical advantage and the second fulcrum corresponds to the second mechanical advantage, the first and second mechanical advantages being different, the trigger engaging the first fulcrum to produce the first mechanical advantage when the second fulcrum is in the first position and the trigger engaging the second fulcrum to produce the second mechanical advantage when the second fulcrum is in the second position.

12. The paste injector gun of claim 11 further including a spring loaded detent adjacent the second fulcrum, the second fulcrum further including a first notch corresponding to the first position and a second notch corresponding to the second position, the detent engaging the first notch when the second fulcrum is in the first position and the second notch when the second fulcrum is in the second position.

13. The paste injector gun of claim 9 further including a rotatable knob connected to the second pivot means such that when the knob is rotated the second pivot means rotates between the first and second position.

14. A paste injector gun for dispensing a paste from a cartridge, the paste injector gun comprising a housing having a U-shaped opening for receiving the cartridge and the paste injector gun further including a gate hinged at one end to the housing, the gate rotatable between an open position in which a cartridge can be positioned in the U-shaped opening and a closed position in which the gate closes the U-shaped opening for positive retention of the cartridge, the gate including a closure tab extending from an end opposite the hinged end and the housing including a tab receiving slot, the closure tab fitting into the tab receiving slot when the gate is in the closed position, and a spring loaded detent is mounted adjacent the tab receiving slot and projects into the tab receiving slot, the closure tab including a depression for receiving the detent when the gate is in the closed position.

15. The paste injector gun of claim 14 wherein the closure tab includes an outwardly extending ear, the ear being shaped to facilitate gripping the gate by a user.

16. The paste injector gun of claim 14 wherein the housing includes first and second U-shaped slots adjacent the U-shaped opening and the gate includes corresponding first and second U-shaped slots aligned with the first and second U-shaped slots in the housing, the first slots being sized to accept a small diameter cement cartridge and the second slots being sized to accept a large diameter cement cartridge.

* * * * *